United States Patent
Hwang et al.

(10) Patent No.: US 11,626,625 B2
(45) Date of Patent: Apr. 11, 2023

(54) APPARATUS FOR REAL-TIME ANALYSIS OF GAS GENERATED INSIDE SECONDARY BATTERY

(71) Applicant: LG Chem, Ltd., Seoul (KR)

(72) Inventors: Dongguk Hwang, Daejeon (KR); Su Hyun Kim, Daejeon (KR); Ji Hye Park, Daejeon (KR); Jeong Ae Ahn, Daejeon (KR); Nak Hee Choi, Daejeon (KR)

(73) Assignee: LG Energy Solution, Ltd.

( * ) Notice: Subject to any disclaimer, the term of this patent is extended or adjusted under 35 U.S.C. 154(b) by 381 days.

(21) Appl. No.: 16/760,178

(22) PCT Filed: May 21, 2019

(86) PCT No.: PCT/KR2019/006056
§ 371 (c)(1),
(2) Date: Apr. 29, 2020

(87) PCT Pub. No.: WO2019/235757
PCT Pub. Date: Dec. 12, 2019

(65) Prior Publication Data
US 2020/0350638 A1 Nov. 5, 2020

(30) Foreign Application Priority Data

Jun. 7, 2018 (KR) .................. 10-2018-0065249
Oct. 30, 2018 (KR) .................. 10-2018-0130852

(51) Int. Cl.
*G01N 33/00* (2006.01)
*G01L 19/00* (2006.01)
(Continued)

(52) U.S. Cl.
CPC .......... *H01M 10/4285* (2013.01); *G01K 1/14* (2013.01); *G01L 19/00* (2013.01);
(Continued)

(58) Field of Classification Search
CPC .... G01N 21/05; G01N 35/0092; G01N 35/00; G01N 33/54313; G01N 33/54366;
(Continued)

(56) References Cited

U.S. PATENT DOCUMENTS 4,078,121 A 3/1978 Gratzmuller
2010/0239895 A1 9/2010 Yang et al.
(Continued)

FOREIGN PATENT DOCUMENTS

CN 101512821 A 8/2009
CN 203850366 U 9/2014
(Continued)

OTHER PUBLICATIONS

European Search Report for Application No. 19815369.4, dated Jan. 21, 2021, 10 pages.
(Continued)

*Primary Examiner* — Andre J Allen
(74) *Attorney, Agent, or Firm* — Lerner, David, Littenberg, Krumholz & Mentlik, LLP (57) ABSTRACT

The present invention relates to a gas analysis apparatus for a secondary battery, the gas analysis apparatus being capable of effectively performing quantitative analysis and qualitative analysis of the gas generated up to the ignition or explosion of the secondary battery.

8 Claims, 5 Drawing Sheets

(51) Int. Cl.
G05D 16/20 (2006.01)
G01K 1/14 (2021.01)
H01M 10/42 (2006.01)
G01R 31/389 (2019.01)

(52) U.S. Cl.
CPC ..... *G01N 33/0036* (2013.01); *G05D 16/2013* (2013.01); *G01R 31/389* (2019.01)

(58) Field of Classification Search
CPC ......... G01N 21/6428; G01N 35/00871; G01N 35/08; G01N 35/1065; G01N 2015/1006; G01N 35/0029; G01N 2035/00326; G01N 21/64; G01N 27/44791; G01N 2035/00356; G01N 33/48721; G01N 2201/062; G01N 33/5438; G01N 35/026; G01N 21/645; G01N 2035/00148; G01N 2035/00495; G01N 35/10; G01N 21/3504; G01N 15/1459; G01N 2035/00158; G01N 2021/6441; G01N 21/76; G01N 2021/6482; G01N 2201/06113; G01N 33/5005; G01N 30/88; G01N 33/497; G01N 35/00732; G01N 35/1011; G01N 15/1484; G01N 33/2823; G01N 27/44743; G01N 30/06; G01N 2035/00435; G01N 27/44704; G01N 2035/00366; G01N 35/0069; G01N 2030/027; G01N 2035/00237; G01N 35/04; G01N 1/405; G01N 2015/1486; G01N 21/6452; G01N 35/1004; G01N 15/1475; G01N 21/78; G01N 27/62; G01N 33/5302; G01N 35/0099; G01N 2035/00752; G01N 33/54373; G01N 21/0303; G01N 21/85; G01N 30/02; G01N 1/31; G01N 21/31; G01N 33/48; G01N 35/1097; G01N 2021/6439; G01N 21/59; G01N 21/65; G01N 27/4145; G01N 27/44721; G01N 33/54306; G01N 33/18; G01N 15/1404; G01N 2015/0073; G01N 30/7233; G01N 1/2205; G01N 2015/008; G01N 2035/1076; G01N 21/03; G01N 35/1095; G01N 1/10; G01N 21/27; G01N 2201/024; G01N 2015/149; G01N 21/25; G01N 2201/08; G01N 2333/96433; G01N 30/72; G01N 35/1002; G01N 35/1072; G01N 1/2035; G01N 1/24; G01N 1/28; G01N 2035/00633; G01N 21/01; G01N 21/274; G01N 2201/061; G01N 2201/0612; G01N 2201/12; G01N 33/92; G01N 35/00623; G01N 21/6486; G01N 2035/00306; G01N 21/6454; G01N 2201/02; G01N 27/327; G01N 33/0009; G01N 1/40; G01N 15/1463; G01N 2021/0346; G01N 2021/058; G01N 2035/00881; G01N 2035/1025; G01N 21/031; G01N 33/0036; G01N 33/57434; G01N 1/14; G01N 2035/00449; G01N 21/253; G01N 2201/0697; G01N 35/025; G01N 2021/6417; G01N 21/6458; G01N 33/4833; G01N 33/80; G01N 1/34; G01N 15/06; G01N 2035/00138; G01N 2035/00425; G01N 2035/0486; G01N 2035/0491; G01N 21/35; G01N 2201/04; G01N 27/745; G01N 30/16; G01N 35/1009; G01N 1/30; G01N 15/14; G01N 2035/0474; G01N 2035/0493; G01N 2035/0494; G01N 21/39; G01N 2201/0621; G01N 31/12; G01N 33/182; G01N 33/56983; G01N 33/62; G01N 33/6827; G01N 1/2202; G01N 2030/8804; G01N 2035/0405; G01N 2035/0444; G01N 33/48707; G01N 33/56966; G01N 2030/628; G01N 2030/8813; G01N 2201/0642; G01N 30/8658; G01N 33/542; G01N 35/00584; G01N 35/1079; G01N 15/00; G01N 2001/007; G01N 2015/0053; G01N 2035/00524; G01N 2035/0441; G01N 2035/0443; G01N 2035/1086; G01N 21/3577; G01N 21/718; G01N 30/6095; G01N 21/8507; G01N 33/6848; G01N 1/2273; G01N 1/26; G01N 1/38; G01N 2021/3595; G01N 2030/067; G01N 2035/1032; G01N 21/07; G01N 2201/0627; G01N 27/447; G01N 27/44756; G01N 33/0011; G01N 33/491; G01N 33/5308; G01N 35/00693; G01N 35/0098; G01N 2015/0065; G01N 2021/399; G01N 2021/6419; G01N 33/487; G01N 35/085; G01N 1/42; G01N 2035/00851; G01N 2458/10; G01N 30/74; G01N 33/50; G01N 33/54386; G01N 2015/0693; G01N 2035/00247; G01N 27/44747; G01N 27/622; G01N 30/7206; G01N 33/49; G01N 33/6893; G01N 1/2226; G01N 2015/0687; G01N 2021/6471; G01N 2035/00465; G01N 21/251; G01N 21/53; G01N 23/223; G01N 24/081; G01N 27/44726; G01N 33/2841; G01N 33/54326; G01N 35/109; G01N 2015/0084; G01N 2021/6421; G01N 2035/00376; G01N 2035/0465; G01N 2035/1051; G01N 21/6445; G01N 2223/076; G01N 27/3271; G01N 27/3277; G01N 2001/2866; G01N 2015/1413; G01N 2021/6432; G01N 2021/6463; G01N 2035/0446; G01N 2201/0646; G01N 27/416; G01N 33/0016; G01N 33/483; G01N 2015/0076; G01N 2015/1087; G01N 2015/1493; G01N 2035/0091; G01N 25/4833; G01N 30/08; G01N 31/22; G01N 33/0031; G01N 33/0032; G01N 33/24; G01N 33/241; G01N 33/5306; G01N 2035/0436; G01N 21/51; G01N 29/036; G01N 30/12; G01N 33/4915; G01N 33/57492; G01N 33/86; G01N 1/2214; G01N 1/286; G01N 1/312; G01N 15/02; G01N 15/0205; G01N 15/1434; G01N 2001/045; G01N 2001/2223; G01N 2015/0003; G01N 2021/8411; G01N 2033/4975; G01N 2035/00386; G01N 2035/0097; G01N 2035/0437; G01N 21/278; G01N 21/75; G01N 2800/367; G01N 33/2888; G01N 33/4905; G01N 33/5029; G01N 33/525; G01N 33/689; G01N 15/065; G01N 2001/021; G01N 2001/4038; G01N 2015/1081; G01N 2021/391; G01N 2021/8557; G01N 2030/025; G01N 2030/8854; G01N 2035/0413; G01N 2035/0415; G01N
21/11; G01N 21/1702; G01N 21/6456;
G01N 2201/0218; G01N 27/308; G01N
1/20; G01N 1/2813; G01N 1/4077; G01N
1/44; G01N 15/1456; G01N 2001/2886;
G01N 2001/4088; G01N 2015/003; G01N
2021/513; G01N 2021/8405; G01N
2035/00811; G01N 21/17; G01N 21/255;
G01N 21/643; G01N 2291/02881; G01N
27/4062; G01N 33/00; G01N 33/004;
G01N 33/1826; G01N 33/2858; G01N
33/5091; G01N 33/582; G01N 33/6875;
G01N 35/00722; G01N 1/2247; G01N
15/1056; G01N 2001/2241; G01N
2015/1018; G01N 2015/1497; G01N
2021/054; G01N 2021/825; G01N
2035/00475; G01N 2035/00742; G01N
2035/0448; G01N 21/0332; G01N 21/33;
G01N 21/6402; G01N 2291/02836; G01N
2333/96466; G01N 24/082; G01N
24/084; G01N 25/4866; G01N 2500/10;
G01N 27/44782; G01N 27/44795; G01N
27/48; G01N 29/2418; G01N 33/0006;
G01N 33/0047; G01N 33/2876; G01N
33/5041; G01N 33/5097; G01N 33/569;
G01N 33/56961; G01N 33/577; G01N
33/68; G01N 33/728; G01N 35/02; G01N
5/04; G01N 1/02; G01N 1/4022; G01N
15/0618; G01N 15/0625; G01N 15/0656;
G01N 15/1436; G01N 2001/2229; G01N
2001/2244; G01N 2001/2267; G01N
2015/0046; G01N 2015/0662; G01N
2021/1704; G01N 2030/525; G01N
2035/00287; G01N 2035/00455; G01N
2035/00702; G01N 2035/00792; G01N
2035/0093; G01N 2035/0453; G01N
2035/1034; G01N 21/359; G01N 21/79;
G01N 21/84; G01N 21/94; G01N
2291/02818; G01N 27/403; G01N
29/222; G01N 30/20; G01N 30/30; G01N
30/34; G01N 33/1886; G01N 33/53;
G01N 33/537; G01N 33/538; G01N
35/00009; G01N 1/22; G01N 1/4044;
G01N 11/04; G01N 15/12; G01N
15/1427; G01N 15/1429; G01N
2001/2217; G01N 2001/4016; G01N
2011/006; G01N 2015/1452; G01N
2021/0112; G01N 2021/7763; G01N
2030/0095; G01N 2030/062; G01N
2030/085; G01N 2030/3007; G01N
2030/8881; G01N 2035/00831; G01N
21/13; G01N 21/314; G01N 21/77;
G01N 21/80; G01N 2201/0231; G01N
2201/0245; G01N 27/12; G01N 27/28;
G01N 27/44786; G01N 27/453; G01N
27/624; G01N 2800/085; G01N 2800/52;
G01N 29/223; G01N 30/78; G01N 30/84;
G01N 33/0037; G01N 33/02; G01N
33/1846; G01N 33/1866; G01N 33/492;
G01N 33/5011; G01N 35/1074; G01N
7/00; G01N 7/10; G01N 7/14; G01N
9/36; G01N 1/2208; G01N 1/2252; G01N
11/00; G01N 13/00; G01N 15/147; G01N
2001/027; G01N 2001/028; G01N
2015/0069; G01N 2015/1093; G01N
2021/0325; G01N 2021/1727; G01N
2021/1761; G01N 2021/177; G01N
2021/392; G01N 2021/6484; G01N
2030/009; G01N 2030/128; G01N
2035/00534; G01N 2035/1048; G01N
21/3151; G01N 21/648; G01N 2223/616;
G01N 2291/0255; G01N 23/04; G01N
23/046; G01N 27/3272; G01N 27/3273;
G01N 27/414; G01N 29/42; G01N
30/461; G01N 30/462; G01N 30/7266;
G01N 30/82; G01N 33/0044; G01N
33/2811; G01N 33/2829; G01N 33/553;
G01N 33/66; G01N 35/021; G01N
35/1016; G01N 5/00; G01N 1/00; G01N
1/08; G01N 15/0255; G01N 2001/002;
G01N 2001/383; G01N 2001/4061; G01N
2015/0288; G01N 2015/1402; G01N
2021/1734; G01N 2030/201; G01N
2030/8411; G01N 2030/8868; G01N
2033/0072; G01N 2033/0093; G01N
2035/00019; G01N 2035/00039; G01N
2035/00059; G01N 2035/00168; G01N
2035/00346; G01N 2035/00396; G01N
2035/0094; G01N 2035/0412; G01N
2035/0475; G01N 2035/1013; G01N
21/3563; G01N 21/49; G01N 21/66;
G01N 2201/0221; G01N 2201/068; G01N
2201/104; G01N 2291/02872; G01N
2291/102; G01N 23/00; G01N 24/08;
G01N 24/085; G01N 25/20; G01N 27/02;
G01N 27/623; G01N 27/64; G01N
29/326; G01N 3/12; G01N 30/28; G01N
30/8668; G01N 31/005; G01N 33/0034;
G01N 33/0042; G01N 33/0057; G01N
33/227; G01N 33/4875; G01N 33/5014;
G01N 33/533; G01N 33/543; G01N
33/54333; G01N 33/552; G01N
33/56972; G01N 33/574; G01N
33/57484; G01N 33/6842; G01N
35/00712; G01N 35/1081; G01N 1/16;
G01N 1/18; G01N 1/4055; G01N
15/0266; G01N 15/0612; G01N 15/0826;
G01N 15/10; G01N 15/1468; G01N
2001/387; G01N 2001/4094; G01N
2015/144; G01N 2015/1481; G01N
2021/0321; G01N 2021/4714; G01N
2021/6491; G01N 2021/8416; G01N
2030/3084; G01N 2035/0425; G01N
2035/1027; G01N 21/15; G01N 21/21;
G01N 21/37; G01N 21/658; G01N
2201/0846; G01N 2223/202; G01N
23/083; G01N 23/12; G01N 2333/70596;
G01N 2333/96455; G01N 25/18; G01N
27/26; G01N 27/4143; G01N 27/4166;
G01N 27/4473; G01N 27/44734; G01N
27/626; G01N 2800/385; G01N 29/02;
G01N 30/36; G01N 30/468; G01N 30/60;
G01N 30/62; G01N 33/006; G01N
33/0062; G01N 33/0073; G01N 33/15;
G01N 33/1833; G01N 33/493; G01N
33/5304; G01N 33/558; G01N 33/559;
G01N 33/566; G01N 33/56911; G01N
33/57496; G01N 33/6845; G01N 33/94;
G01N 1/2211; G01N 1/2258; G01N
11/02; G01N 15/0211; G01N 15/0227;

G01N 15/05; G01N 15/1012; G01N 2001/2057; G01N 2001/2071; G01N 2001/2264; G01N 2001/2276; G01N 2001/2282; G01N 2001/2826; G01N 2001/4066; G01N 2001/4083; G01N 2009/006; G01N 2011/008; G01N 2013/003; G01N 2015/0007; G01N 2015/0011; G01N 2015/1477; G01N 2015/1488; G01N 2021/1738; G01N 2021/4742; G01N 2021/6478; G01N 2021/653; G01N 2030/121; G01N 2030/126; G01N 2030/143; G01N 2030/3046; G01N 2030/484; G01N 2030/521; G01N 2030/524; G01N 2030/746; G01N 2030/8405; G01N 2030/8809; G01N 2030/8822; G01N 2035/00049; G01N 2035/00564; G01N 2035/00683; G01N 2035/0401; G01N 2035/103; G01N 21/09; G01N 21/3581; G01N 21/4133; G01N 21/47; G01N 21/474; G01N 21/532; G01N 21/553; G01N 21/5907; G01N 21/62; G01N 21/6408; G01N 21/71; G01N 21/7743; G01N 21/7746; G01N 2201/0826; G01N 2201/0833; G01N 2201/084; G01N 2201/125; G01N 2201/129; G01N 2291/02466; G01N 23/207; G01N 2333/415; G01N 2333/43534; G01N 2333/70589; G01N 2560/00; G01N 27/045; G01N 27/22; G01N 27/221; G01N 27/3274; G01N 27/66; G01N 29/024; G01N 30/00; G01N 30/14; G01N 30/24; G01N 30/38; G01N 30/46; G01N 30/50; G01N 30/6043; G01N 30/6052; G01N 30/66; G01N 30/722; G01N 30/86; G01N 30/8675; G01N 31/00; G01N 31/16; G01N 31/221; G01N 33/0014; G01N 33/0049; G01N 33/0052; G01N 33/0063; G01N 33/025; G01N 33/146; G01N 33/205; G01N 33/28; G01N 33/2805; G01N 33/4925; G01N 33/4972; G01N 33/5085; G01N 33/521; G01N 33/544; G01N 33/551; G01N 33/588; G01N 33/6803; G01N 33/6818; G01N 33/6854; G01N 33/723; G01N 5/02; G01N 9/002; G01N 1/125; G01N 1/36; G01N 15/0272; G01N 15/0606; G01N 15/1431; G01N 2001/1427; G01N 2001/205; G01N 2001/242; G01N 2001/382; G01N 2001/388; G01N 2011/0046; G01N 2015/0038; G01N 2015/0092; G01N 2015/0216; G01N 2015/025; G01N 2015/0261; G01N 2015/1075; G01N 2021/0106; G01N 2021/258; G01N 2021/317; G01N 2021/3174; G01N 2021/4711; G01N 2021/4716; G01N 2021/4719; G01N 2021/656; G01N 2021/8528; G01N 2030/122; G01N 2030/125; G01N 2030/285; G01N 2030/3015; G01N 2030/303; G01N 2030/376; G01N 2030/8417; G01N 2030/8831; G01N 2030/884; G01N 2030/965; G01N 2035/00099; G01N 2035/00108; G01N 2035/00277; G01N 2035/00445; G01N 2035/00485; G01N 2035/00772; G01N 2035/00841; G01N 2035/0403; G01N 2035/042; G01N 2035/0422; G01N 2035/0477; G01N 2035/0482; G01N 2035/1062; G01N 21/23; G01N 21/272; G01N 21/276; G01N 21/293; G01N 21/3103; G01N 21/41; G01N 21/4738; G01N 21/69; G01N 21/714; G01N 21/763; G01N 21/8483; G01N 21/8851; G01N 21/9501; G01N 2201/021; G01N 2201/025; G01N 2201/1087; G01N 2201/1214; G01N 2201/1215; G01N 2201/127; G01N 2201/1296; G01N 2203/0222; G01N 2203/0282; G01N 2203/0494; G01N 2223/1016; G01N 2223/401; G01N 2333/395; G01N 2333/7454; G01N 2333/96447; G01N 2458/15; G01N 2500/02; G01N 2570/00; G01N 27/04; G01N 27/18; G01N 27/3276; G01N 27/4071; G01N 27/44708; G01N 27/44773; G01N 27/70; G01N 2800/22; G01N 2800/26; G01N 29/04; G01N 3/10; G01N 30/0005; G01N 30/6047; G01N 30/606; G01N 30/6091; G01N 30/64; G01N 30/7273; G01N 30/76; G01N 30/8682; G01N 30/90; G01N 30/96; G01N 33/0004; G01N 33/0022; G01N 33/0027; G01N 33/0098; G01N 33/10; G01N 33/1813; G01N 33/2835; G01N 33/48728; G01N 33/48735; G01N 33/48785; G01N 33/5008; G01N 33/5047; G01N 33/536; G01N 33/58; G01N 33/64; G01N 33/6812; G01N 33/726; G01N 33/946; G01N 33/9486; G01N 1/06; G01N 1/2294; G01N 1/4005; G01N 11/14; G01N 11/142; G01N 13/04; G01N 15/0637; G01N 15/1209; G01N 17/002; G01N 2001/1031; G01N 2001/1037; G01N 2001/1043; G01N 2001/105; G01N 2001/1075; G01N 2001/2279; G01N 2001/2288; G01N 2001/2291; G01N 2001/248; G01N 2001/305; G01N 2011/0006; G01N 2015/0057; G01N 2015/0277; G01N 2015/0294; G01N 2015/084; G01N 2015/0846; G01N 2015/1272; G01N 2015/1415; G01N 2015/142; G01N 2021/0118; G01N 2021/015; G01N 2021/0389; G01N 2021/052; G01N 2021/056; G01N 2021/154; G01N 2021/1723; G01N 2021/3107; G01N 2021/3166; G01N 2021/3177; G01N 2021/394; G01N 2021/4707; G01N 2021/4709; G01N 2021/651; G01N 2021/7759; G01N 2021/7796; G01N 2021/8472; G01N 2021/855; G01N 2027/222; G01N 2030/003; G01N 2030/0035; G01N 2030/042; G01N 2030/165; G01N 2030/202; G01N 2030/207; G01N 2030/3038; G01N 2030/3053; G01N 2030/562; G01N 2030/625; G01N 2030/642; G01N 2030/765; G01N 2030/8886; G01N 2033/4977; G01N 2035/00089; G01N 2035/00504; G01N

2035/00514; G01N 2035/00554; G01N 2035/00673; G01N 2035/00801; G01N 2035/00861; G01N 2035/0406; G01N 2035/0427; G01N 2035/0439; G01N 2035/1018; G01N 21/0317; G01N 21/1717; G01N 21/3518; G01N 21/552; G01N 21/6404; G01N 21/67; G01N 21/72; G01N 21/73; G01N 21/74; G01N 21/86; G01N 21/8903; G01N 21/898; G01N 2201/0227; G01N 2201/0228; G01N 2201/023; G01N 2201/0636; G01N 2201/064; G01N 2201/0696; G01N 2201/088; G01N 2201/1211; G01N 2223/01; G01N 2223/04; G01N 2223/074; G01N 2223/304; G01N 2223/419; G01N 2223/605; G01N 2223/6116; G01N 2223/635; G01N 2223/637; G01N 2223/638; G01N 2291/021; G01N 2291/0256; G01N 2291/0427; G01N 23/06; G01N 23/085; G01N 23/20008; G01N 23/20025; G01N 23/2204; G01N 23/222; G01N 23/2254; G01N 2333/59; G01N 2333/805; G01N 2333/908; G01N 2474/20; G01N 25/00; G01N 25/04; G01N 25/22; G01N 25/48; G01N 25/4873; G01N 27/00; G01N 27/06; G01N 27/07; G01N 27/124; G01N 27/14; G01N 27/16; G01N 27/225; G01N 27/226; G01N 27/333; G01N 27/4045; G01N 27/4075; G01N 27/4076; G01N 27/413; G01N 27/4163; G01N 27/44717; G01N 27/74; G01N 2800/387; G01N 29/022; G01N 29/0609; G01N 29/0645; G01N 29/069; G01N 29/11; G01N 29/14; G01N 29/226; G01N 29/2425; G01N 3/04; G01N 3/32; G01N 30/10; G01N 30/18; G01N 30/465; G01N 30/467; G01N 30/56; G01N 30/6026; G01N 30/80; G01N 30/8665; G01N 31/10; G01N 31/164; G01N 31/227; G01N 33/0013; G01N 33/0018; G01N 33/0059; G01N 33/0065; G01N 33/0067; G01N 33/007; G01N 33/0075; G01N 33/04; G01N 33/12; G01N 33/22; G01N 33/26; G01N 33/48771; G01N 33/48792; G01N 33/5094; G01N 33/56916; G01N 33/581; G01N 33/585; G01N 33/6809; G01N 33/6851; G01N 33/6872; G01N 33/98; G01N 35/00663; G01N 35/0095; G01N 35/028; G01N 7/18; G01N 9/30

See application file for complete search history.

(56) References Cited

U.S. PATENT DOCUMENTS

2015/0064514 A1  3/2015  Wu et al.
2015/0079436 A1  3/2015  Chung et al.

FOREIGN PATENT DOCUMENTS

| | | | |
|---|---|---|---|
| JP | H09147927 A | 6/1997 | |
| JP | 2008039459 A | 2/2008 | |
| JP | 2009081059 A | 4/2009 | |
| JP | 2012138323 A | 7/2012 | |
| JP | 5050845 B2 | 10/2012 | |
| JP | 2013080634 A | 5/2013 | |
| JP | 2016534518 A | 11/2016 | |
| JP | 2017101926 A | 6/2017 | |
| JP | 2017181212 A | 10/2017 | |
| KR | 20080023375 A | 3/2008 | |
| KR | 100832245 B1 | 5/2008 | |
| KR | 20120050667 A | 5/2012 | |
| KR | 20120111080 A | 10/2012 | |
| KR | 20150032034 A | 3/2015 | |
| KR | 20150053199 A | 5/2015 | |
| KR | 20160066909 A | 6/2016 | |
| KR | 20160072571 A | 6/2016 | |
| KR | 20160081394 A * | 7/2016 | ............ H01M 50/30 |
| KR | 101760401 B1 | 7/2017 | |
| KR | 20180047359 A | 5/2018 | |
| WO | WO-2019083207 A1 * | 5/2019 | ........ H01M 10/4207 |
| WO | WO-2020218785 A1 * | 10/2020 | ............... G01N 1/22 |

OTHER PUBLICATIONS

Search Report dated Dec. 9, 2021 from the Office Action for Chinese Application No. 201980005418.2 dated Dec. 17, 2021, 3 pages.

International Search Report for Application No. PCT/KR2019/006056 dated Aug. 23, 2019, 2 pages.

"Security Management Technology", written by Changming Yuan, p. 272, published by Metallurgical Industry Press on Mar. 2009. 4 pgs.

Search Report dated May 11, 2022 from the Office Action for Chinese Application No. 201980005418.2 dated May 20, 2022 2 pages . . . (see p. 1, categorizing the cited reference).

* cited by examiner

APPARATUS FOR REAL-TIME ANALYSIS OF GAS GENERATED INSIDE SECONDARY BATTERY

CROSS-REFERENCE TO RELATED APPLICATIONS

This application is a national phase entry under 35 U.S.C. § 371 of International Patent Application No. PCT/KR2019/006056, filed on May 21, 2019, which claims priority from Korean Patent Application Nos. 10-2018-0065249, filed on Jun. 7, 2018, and 10-2018-0130852, filed on Oct. 30, 2018, the entire disclosures of which are hereby incorporated herein by reference.

BACKGROUND OF THE INVENTION

1. Field of the Invention

The present invention relates to a gas analysis device for a secondary battery, and more particularly, to an analysis device capable of effectively performing a quantitative analysis and qualitative analysis of generated gas up to the point of ignition or explosion of the secondary battery.

2. Description of the Related Art

In general, a secondary battery is a battery that can be repeatedly used through a discharge process of converting chemical energy into electrical energy and a charging process in the reverse direction thereof. The secondary battery having electric properties such as high application ability to product groups and high energy density is commonly used in electric vehicles (EVs) or hybrid vehicles (HVs) driven by electric driving sources as well as portable devices.

In collecting and analyzing the generated gas in the secondary battery, various gases are generated during operation of the secondary battery. The information on the composition and content of the generated gas in the secondary battery may be used for developing battery materials, optimizing battery manufacturing processes, and identification of the cause of battery failure.

However, the secondary battery has a risk of ignition/explosion when exposed to high temperatures. In addition, even when a large current flows within a short time due to overcharge, external short circuit, nail penetration, local crush, or the like, there is a risk of ignition/explosion while the battery is heated by IR heating. As an example, as a result of the reaction between electrolyte and electrodes, gas is generated to increase internal battery pressure, and the secondary battery may explode at a pressure equal to or greater than a predetermined pressure.

In addition, a serious problem may occur such as a swelling phenomenon of a battery or a battery igniting or exploding due to an increase in pressure in a chamber in which a secondary battery is mounted due to a temperature rise and a gas generated during a secondary battery experiment. When the battery is ignited or exploded, the analysis device is exposed to the risk of damage due to flame, dust, and high-pressure gas. Therefore, there is a need for a device for analyzing a generated gas in a secondary battery in real time until the point of ignition or explosion of the secondary battery, and furthermore a device that can be applied to experiments related to safety evaluation (overcharge, high temperature exposure, etc.).

In addition, the need for experiments related to safety evaluation (overcharge, high temperature exposure, etc.) of the current secondary battery is increasing. Therefore, a solution for securing researchers' safety and protecting an analytical device from the risk of battery ignition and explosion is required for a case in that the battery is overcharged and exposed to high temperature.

SUMMARY OF THE INVENTION

Therefore, the present invention is to solve the above problems. An object of the present invention is to provide a device for analyzing the generated gas in real time up to the point of ignition and explosion, while securing researchers' safety and protecting an analytical device of the generated gas in the secondary battery from the risk of battery ignition and explosion.

A device for analyzing the generated gas in the secondary battery according to the present invention comprises:
a chamber in which the secondary battery is mounted;
an induction medium supply module for generating a flow of induction medium into the chamber; and
an analysis module for analyzing the generated gas in the secondary battery introduced from the chamber by the flow of the induction medium,
wherein the chamber comprises:
an inlet to which the induction medium supply module is connected;
an outlet to which the analysis module is connected; and
a safety valve for releasing flame, dust, and high-pressure gas generated during explosion or ignition of the secondary battery to the outside.

Effect of the Invention

According to the present invention, there is provided a device for analyzing a generated gas in a secondary battery in real time up to the point of ignition and explosion of the secondary battery, while securing researchers' safety and protecting an analytical device of the generated gas in the secondary battery from the risk of battery ignition and explosion.

Furthermore, in addition to the real-time analysis of the generated gas in the secondary battery, it can be applied to experiments related to safety evaluation (overcharge, high temperature exposure, etc.) and analysis of the secondary battery until after ignition and explosion.

DETAILED DESCRIPTION OF THE INVENTION

A device for analyzing a generated gas in a secondary battery according to the present invention comprises:

a chamber in which the secondary battery is mounted;

an induction medium supply module for generating a flow of induction medium into the chamber; and an analysis module for analyzing the generated gas in the secondary battery introduced from the chamber by the flow of the induction medium, wherein the chamber comprises:

an inlet to which the induction medium supply module is connected;

an outlet to which the analysis module is connected; and a safety valve for releasing flame, dust, and high-pressure gas generated during explosion or ignition of the secondary battery to the outside.

In addition, the device for analyzing the generated gas in the secondary battery according to the present invention may further comprise:

a first shutoff valve connected between the inlet and the chamber; and a second shutoff valve connected between the outlet and the chamber, wherein the first shutoff valve may shut off a flow of fluid from the chamber to the induction medium supply module when the secondary battery is exploded or ignited, and the second shut-off valve may shut off a flow of fluid from the chamber to the analysis module when the secondary battery is exploded or ignited.

In addition, in the device for analyzing the generated gas in the secondary battery according to the present invention, the first shutoff valve and the second shutoff valve may be switched to a closed state at a pressure equal to or greater than a predetermined pressure, and the safety valve may be switched to an open state at a pressure equal to or greater than a predetermined pressure.

In addition, in the device for analyzing the generated gas in the secondary battery according to the present invention, the first shutoff valve and the second shutoff valve may be automatically switched to a closed state when directly contacting to the gas of the pressure equal to or greater than a predetermined pressure, and the safety valve may be switched to an open state when directly contacting to the gas of the pressure equal to or greater than a predetermined pressure.

In addition, the device for analyzing the generated gas in the secondary battery according to the present invention may further comprise:

a pressure gauge for measuring pressure of the surface of the secondary battery or pressure inside the chamber; and a control unit for immediately transmitting control signals for closing the first shutoff valve, closing the second shutoff valve and opening the safety valve to the first shutoff valve, the second shutoff valve, and the safety valve, respectively, upon receiving a signal indicating that the pressure measured by the pressure gauge is equal to or greater than a predetermined pressure, wherein, according to the control signal of the control unit, the first shutoff valve and the second shutoff valve may be switched to a closed state and the safety valve may be switched to an open state.

In addition, the device for analyzing the generated gas in the secondary battery according to the present invention may further comprise:

a temperature sensor for measuring temperature of the surface of the secondary battery or temperature inside the chamber; and a control unit for immediately transmitting control signals for closing the first shutoff valve, closing the second shutoff valve and opening the safety valve to the first shutoff valve, the second shutoff valve, and the safety valve, respectively, upon receiving a signal indicating that the temperature measured by the temperature sensor is equal to or greater than a predetermined temperature, wherein, according to the control signal of the control unit, the first shutoff valve and the second shutoff valve may be switched to a closed state and the safety valve may be switched to an open state.

In addition, in the device for analyzing the generated gas in the secondary battery according to the present invention, the chamber may further comprise charging/discharging terminals for contacting electrodes of the secondary battery, wherein the device may further comprise a charge/discharge module electrically connected to the electrodes of the secondary battery through the charging/discharging terminals to charge/discharge the secondary battery.

In addition, in the device for analyzing the generated gas in the secondary battery according to the present invention, the chamber may comprise a chamber body in which the secondary battery may be mounted and which has a cuboid shape with an open front portion and a chamber cover adapted to shield the opening, wherein the inlet may be disposed on one side of the chamber body, the outlet may be disposed on the other side of the chamber body, and the safety valve may be disposed at the center of the chamber body.

In addition, in the device for analyzing the generated gas in the secondary battery according to the present invention, the predetermined pressure may be any one of the pressure value in the range of 0.5 Bar to 5 Bar.

Hereinafter, the device for analyzing the generated gas in the secondary battery until ignition or explosion according to an embodiment of the present invention will be described in detail. The accompanying drawings show exemplary forms of the present invention, which are provided to explain the present invention in more detail, and the technical scope of the present invention is not limited thereto.

In addition, irrespective of graphic symbols, the same or corresponding components will be given for the same reference numerals, and redundant description thereof will be omitted and for the convenience of description, the size and shape of each component shown may be exaggerated or reduced.

Figure 1:
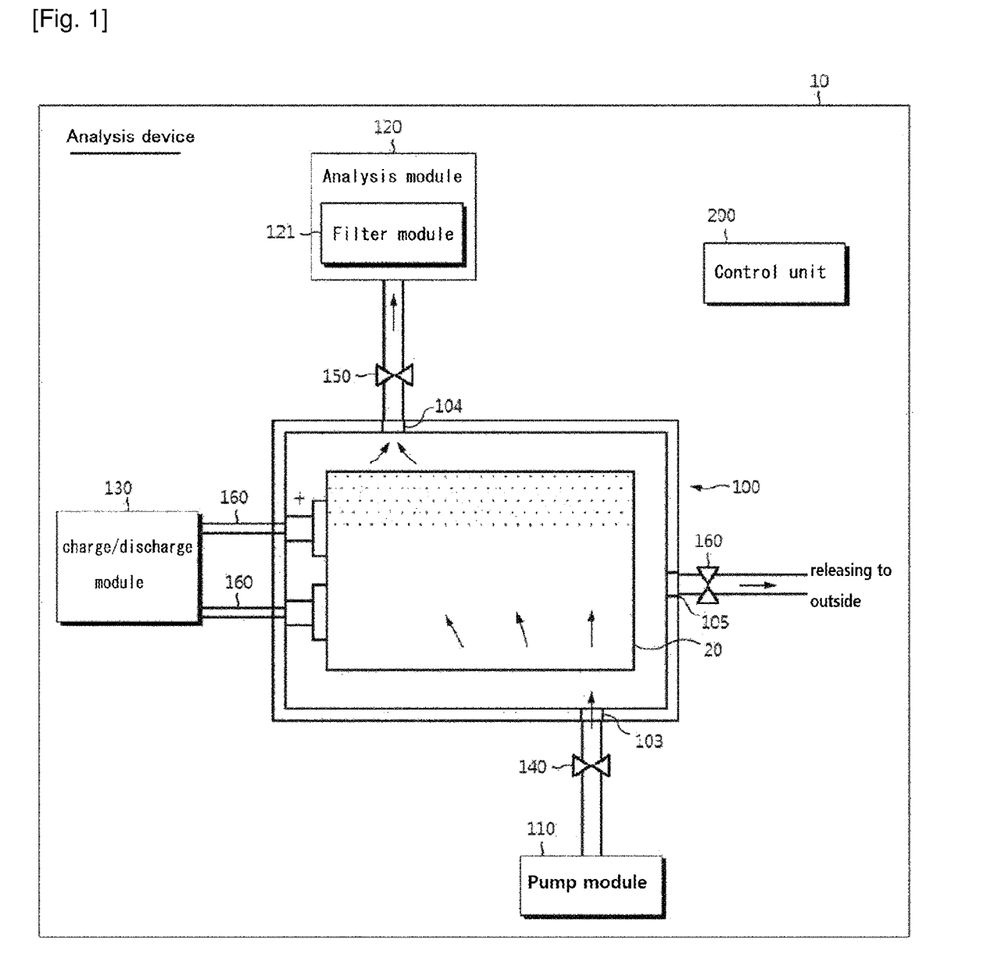
FIG. 1 is a schematic diagram of a device 10 for analyzing the generated gas in the secondary battery according to the present invention.
Figure 2:
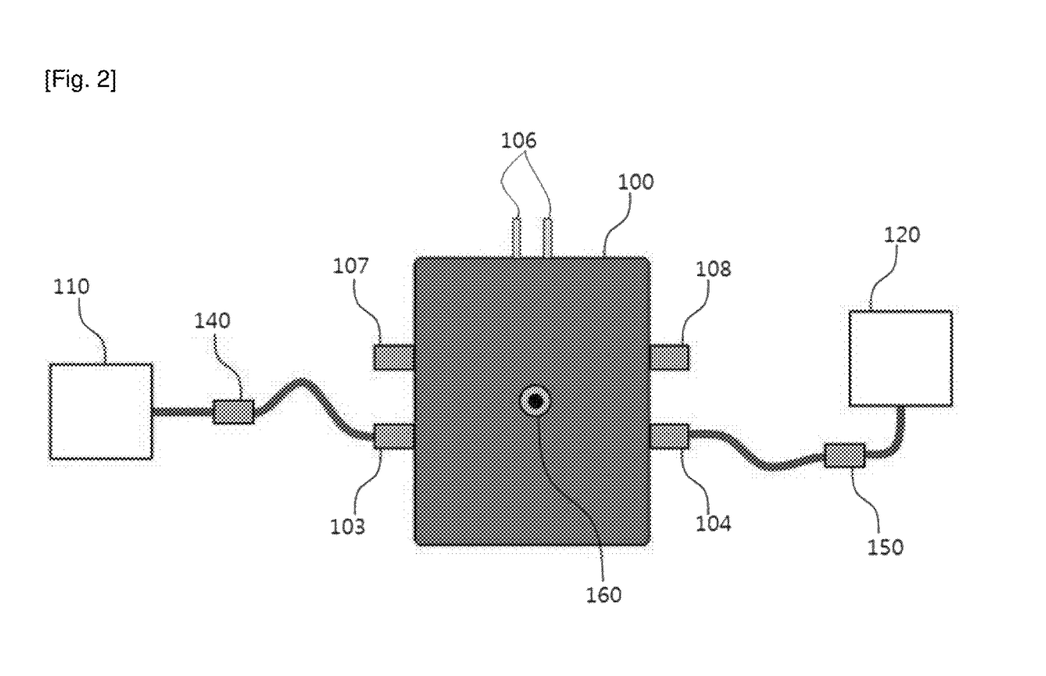
FIG. 2 shows a front view of an example of a device 10 for analyzing the generated gas in the secondary battery according to the present invention.
Figure 3:
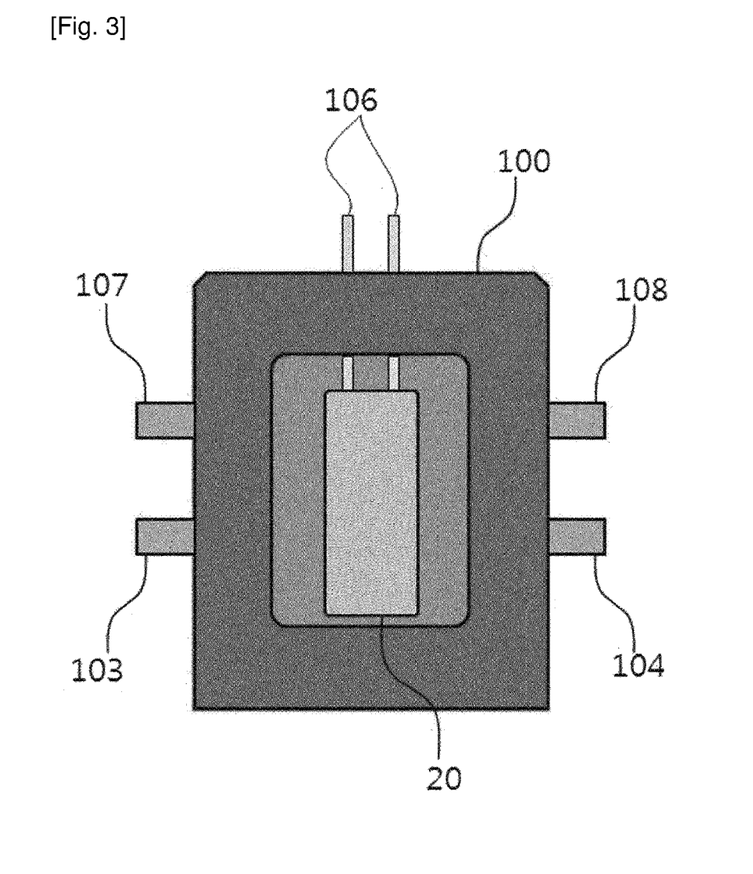
FIG. 3 shows a front view of a main part of the device 10 for analyzing a generated gas in a secondary battery of FIG. 2.

FIG. 1 is a schematic diagram of a device 10 for analyzing a generated gas in a secondary battery according to the present invention. FIG. 2 shows a front view of an example of a device 10 for analyzing a generated gas in a secondary battery according to the present invention. FIG. 3 shows a front view of a main part of the device 10 for analyzing a generated gas in a secondary battery of FIG. 2.

First, referring to FIG. 1, the device 10 for analyzing a generated gas in a secondary battery comprises a chamber 100 in which the secondary battery 20 is mounted, an induction medium supply module 110, and an analysis module 120.

The secondary battery 20 may be a can type (cylindrical, cuboid, etc.), pouch type, or coin cell type secondary battery. The secondary battery 20 may be charged or discharged by an electrochemical reaction of an active material, a metal plate, and an electrolyte, and the like. During such charge or discharge driving, an internal gas may be generated by internal electrochemical reactions.

The secondary battery 20 may be mounted in the chamber 100. Referring to FIG. 3, the chamber 100 includes a chamber body 101 and a chamber cover 102. The chamber body 101 may have a cuboid shape with an open front portion, for example, and the chamber cover 102 may be provided to shield the opening of the chamber body 101. The chamber body 101 and the chamber cover 102 may be tightly coupled by fixing means such as fixing pins, screws and bolts. The contact surface between the chamber body 101 and the chamber cover 102 may further comprise a sealing member such as an O-ring for sealing when the chamber body 101 and the chamber cover 102 are coupled to each other. The chamber body 101 and the chamber cover 102 may each have a dual structure. More specifically, the chamber 100 in which the chamber body 101 and the chamber cover 102 are coupled has a dual structure. In the chamber 100 in which the chamber body 101 and the chamber cover 102 are coupled, the inner surface on which the secondary battery 20 is mounted is made of an insulating and adiabatic material which is durable at high temperature and high pressure. It may be made of bakelite, Teflon, aerosol, or the like. The outer surface surrounding the inner surface may be made of a material such as SUS and metal.

The chamber 100 is provided with an inlet 103 to which the induction medium supply module 110 can be connected and an outlet 104 to which the analysis module 120 can be connected.

The induction medium supply module 110 introduces the induction medium comprising an inert gas or the like into the chamber 100 through the inlet 103 provided in the chamber 100. The induction medium supply module 110 includes a device for moving a gas medium such as a mass flow meter (MFC), a regulator, and the like. The induction medium supply module 110 and the inlet 103 are connected to the induction pipe so that gas flow can be generated. The induction medium comprising an inert gas or the like is preferably composed of an inert gas such as helium, nitrogen, argon, etc. However, the gas component constituting the induction medium may be appropriately selected depending on the component of the generated gas in the secondary battery to be detected and the purpose of analyzing the generated gas in the secondary battery.

By controlling the flow rate in the induction medium supply module 110, the induction medium may be strongly introduced into the chamber 100, and the induction medium introduced into the chamber 100 exit the chamber 100 through the outlet 104 due to the pressure difference between the inlet 103 and the outlet 104 of the chamber 100. By such a transfer flow of the induction medium, the internal generated gas in the secondary battery 20 is transferred to the analysis module 120 through the outlet 104 together with the induction medium.

The analysis module 120 is connected to the outlet 104 provided in the chamber 100 by an induction pipe so that a moving flow of gas discharged from the outlet 104 provided in the chamber 100 can be generated. The analysis module 120 may comprise a filter module 121 for filtering the induction medium. FIG. 1 and FIG. 2 illustrate the case in which the analysis module 120 is connected to the chamber 100 through the induction pipe. If desired, a gas collecting tube (not shown) for collecting the generated gas in the secondary battery may be connected to the outlet 104, and after the collection of the generated gas in the secondary battery, the gas collecting tube may be connected to the analysis module 120 to perform the analysis.

In one embodiment, the inlet 103 is disposed on one side of the chamber body 101 and the outlet 104 is disposed on the other side of the chamber body 101, so that the flow of gas generated until just before ignition or explosion of the secondary battery 20 can be smoothly formed in one direction in the order of the induction medium supply module 110—the chamber 100—the analysis module 120. In FIG. 2, when the chamber 100 is viewed from the front, an inlet 103 to which the induction medium supply module 110 is connected is located on the left side, and an outlet 104 to which the analysis module 120 is connected is located on the right side. However, the present invention is not limited to that shown in FIG. 2 with respect to the position of the inlet 103 and the outlet 104, and various variations and modifications are possible as long as the flow of gas can be formed in the order of the induction medium supply module 110—the chamber 100—the analysis module 120.

In addition, the device 10 for analyzing the generated gas in the secondary battery of the present invention may further comprise a charge/discharge module. That is, since the secondary battery 20 may explode or ignite not only due to charging and discharging, but also due to high temperature or external impact, the device 10 for analyzing the generated gas in the secondary battery according to the present invention may be implemented without the charge/discharge module 130, or since the secondary battery 20 may explode and ignite due to overcharge the device may be implemented with the charge/discharge module 130. The charge/discharge module 130 is electrically connected to the electrodes of the secondary battery to drive the charge/discharge of the secondary battery 20. The charge/discharge module 130 includes a power supply unit, a load unit, and a switching circuit. The power supply unit regulates the voltage and/or current to charge the secondary battery 20, and the load unit discharges the energy charged in the secondary battery 20. The power supply unit and the load unit may be electrically connected to the secondary battery 20 through the charging/discharging terminals 106. The charging/discharging terminals 106 may be provided in the chamber 100 and contact the electrodes of the secondary battery 20. The power supply unit and the load unit may be electrically connected to the secondary battery 20 selectively by a switching circuit. The charge/discharge module 130 may be configured to be controlled by a user signal input through an interface means such as a computer of the user.

In the device 10 for analyzing the generated gas in the secondary battery, when the secondary battery 20 is charged or discharged, there may be explosion or ignition of the secondary battery 20 in the case of exposure of the secondary battery 20 to high temperatures, a short-circuit phenomenon of the positive and negative electrodes of the secondary battery 20, a crush of the secondary battery 20, a nail of the secondary battery 20, and the like. In order to prevent flame, dust, high-pressure gas due to explosion or ignition of the secondary battery 20 form moving to the induction medium supply module 110 and the analysis module 120, the device 10 for analyzing the generated gas in the secondary battery according to the present invention comprises a first shutoff valve 140 provided between the inlet 103 and the induction medium supply module 110, and a second shutoff valve 150 provided between the outlet 104 and the analysis module 120. The first shutoff valve 140 and the second shutoff valve 150 are open/closed according to the pressure inside the chamber 110.

More specifically, in the explosion or ignition of the secondary battery 20, the pressure of the flame, dust, high-pressure gas due to explosion or ignition of the secondary battery 20 may be greater than the pressure of the induction medium delivered into the chamber 100 through the induction medium supply module 110. The first shutoff valve 140 is open, and when the pressure in the chamber 100 becomes higher than a predetermined pressure the first shutoff valve 140 is automatically closed (shut off) in order to prevent damage the induction medium supply module 110 in case that the flame, dust, and high-pressure gas due to explosion or ignition of the secondary battery 20 is moved to the induction medium supply module 110.

The second shutoff valve 150 is open, and when the pressure in the chamber 100 becomes higher than a predetermined pressure the second shutoff valve 150 is automatically closed (shut off) in order to prevent damage the analysis module 120 in case that the flame, dust, and high-pressure gas due to explosion or ignition of the secondary battery 20 is moved to the analysis module 120.

In addition, the device 10 for analyzing the generated gas in the secondary battery may further comprise a safety valve to discharge flame, dust, and high-pressure gas generated during explosion or ignition of the secondary battery 20 to the outside of the device 10 instead of the analysis module 120. The safety valve connection hole 105 may be provided in the chamber 100, and the safety valve 160 may be provided in the safety valve connection hole 105. FIG. 2 exemplarily illustrates a case in which the safety valve 160 is provided at the center of the chamber cover 102 of the chamber 100. This is to minimize the pressure or the flame caused by the ignition and explosion of the secondary battery 20 which is moved to another place when the secondary battery 20 is mounted at the center of the chamber 100. That is, by opening the safety valve 160 at the position closest to the secondary battery 20, the high-pressure gas and the flame inside the chamber 100 may be rapidly released to the outside with low pressure through the safety valve 160. In fact, after ignition of the secondary battery 20 and release of high-pressure gas inside the chamber 100, it can be seen that a hole on the surface of the secondary battery 20 is formed at a position corresponding to the position of the safety valve 160 (where it is in contact with the safety valve 160). The present invention is not limited to the above, and various modifications and changes are possible as long as it can quickly release flame, dust, and high-pressure gas generated during explosion or ignition of the chamber 100, for example when the mounting position of the secondary battery 20 is changed in the chamber 100, the position of the safety valve 160 may be changed accordingly, and the safety valve 160 may be provided in the chamber body 101.

The safety valve 160 is closed, and when the pressure in the chamber 100 becomes higher than a predetermined pressure, the safety valve 160 is automatically opened in order to release flame, dust, and high-pressure gas generated during explosion or ignition of the chamber 100.

For example, the pressure inside the chamber 100 due to the flow of the induction medium from the induction medium supply module 110 during the analysis of the gas generated in real time before the ignition of the secondary battery 20 may be between 1.0 Bar and 1.5 Bar. The predetermined pressure such that the first shutoff valve 140 and the second shutoff valve 150 are automatically closed and the safety valve 160 is automatically opened may be any one of the pressure value in the range of 0.5 Bar to 5 Bar or 1.5 Bar to 2 Bar. The predetermined pressure such that the first shutoff valve 140 and the second shutoff valve 150 are automatically closed and the safety valve 160 is automatically opened is not limited to the above-described value, and is adjustable according to various environments in which the present invention is implemented.

The first shutoff valve 140, the second shutoff valve 150, and the safety valve 160 may be made of a material such as SUS or metal materials to withstand high temperature and high pressure due to explosion or ignition of the secondary battery 20 and may be a valve provided with additional components such as an O-ring. In addition, the first shutoff valve 140, the second shutoff valve 150, and the safety valve 160 may be a valve that can be opened and closed automatically without a driving source (for example, a voltage source), or may be a valve that can be opened and closed automatically with being connected to a separate driving source. As a valve that can be opened and closed automatically without a driving source, a valve that automatically shuts off when a high-pressure gas generated during ignition or explosion of the secondary battery 20 directly contacts the valve can be used. For example, the first shutoff valve 140 and the second shutoff valve 150 may include a check valve, a shut-off valve, a quick closing valve and a cut-off valve, which are capable of blocking the flow of gas and dust. As the safety valve 160, a relief valve or the like may be used.

The chamber 100 may further comprise a first connection hole 107 and/or a second connection hole 108. A temperature sensor to be described later may be disposed in the chamber 100 through the first connection hole 107 and/or the second connection hole 108.

In addition, the chamber 100 further comprises a pressure gauge (not shown) for measuring pressure of the surface of the secondary battery 20 or pressure inside the chamber 100 and a temperature sensor (not shown) for measuring temperature of the surface of the secondary battery 20 or temperature inside of the chamber 100, in a configuration for measuring pressure and temperature of the surface of the secondary battery 20 or inside chamber 100. The pressure gauge may measure the pressure inside the chamber 100 and transmit the measured pressure to the control unit 200 in real time. The pressure gauge may be installed as close as possible to the secondary battery 20 in the chamber 100 so that it is possible to capture the time of ignition and explosion of the secondary battery 20 more quickly. In addition, the temperature sensor may transmit the temperature of the surface of the secondary battery 20 or the temperature inside the chamber 100 to the control unit 200 in real time. The temperature sensor may also be mounted on the surface of the secondary battery 20 or be installed as close as possible to the secondary battery 20. The temperature sensor may be, for example, in the form of a line (for example, a kind of wire coated with insulators on copper). The line-shaped temperature sensor is disposed through the first connection hole 107 or the second connection hole 108 so that one end of the line-shaped temperature sensor is mounted on the surface of the secondary battery 20 and the other end of the temperature sensor is connected to the control unit 200 or a data storage device. If it is desired to measure the temperature at a specific location inside the chamber, one end of the temperature sensor may be disposed at a specific location inside the chamber. Since the temperature sensor installed in the chamber 100 is destroyed by direct damage when the secondary battery 20 is ignited or exploded, use of such a line-shaped temperature sensor may reduce the costs. In addition, such a line-shaped temperature sensor has the advantage that it is very easy to replace. Meanwhile, the data storage device may be a data logger, for example. The data logger is widely used to read temperatures, cell voltages, etc. In addition to the above, various modifications and changes are possible, such as the addition of sensor equipment to the chamber 20. The pressure information measured by the pressure gauge and/or the temperature information measured by the temperature sensor may be stored in the data storage device embedded or separately provided in the control unit 200. In addition to the pressure gauge and/or the temperature sensor, a measuring device or a sensor for measuring the pressure of the secondary battery 20, the resistance, the generation time of the generated gas in the secondary battery 20, the amount of generated gas in the secondary battery 20, and the amount of heat generated by the secondary battery 20 may be mounted in the chamber 100. The measured data may be transmitted to the control unit 200 and/or the data storage device. Any measurement to be performed in other safety tests for secondary battery can be performed at the same time. Through the pressure information measured by the pressure gauge, the temperature information measured by the temperature sensor, the pressure of the secondary battery 20, the resistance, the generation time of the generated gas in the secondary battery 20, the amount of generated gas in the secondary battery 20, and the amount of heat generated by the secondary battery 20, it is possible to obtain the conditions of temperature and pressure, etc. at the time of ignition or explosion of the secondary battery 20, and such information may be used for safety evaluation test of the secondary battery 20.

Additionally, an oven may be provided outside the chamber 100 to apply heat to the chamber 100 or the chamber 100 itself includes a device capable of directly heating the chamber 100, thereby raising the temperature of the secondary battery 20. In order to be utilized not only in case of ignition or explosion of the secondary battery 20, but also in the safety evaluation test of the secondary battery 20, it is also possible to apply a low temperature (cooler, liquid nitrogen, etc.) to an external low-temperature oven or chamber in the same manner as the safety evaluation test of the secondary battery 20.

If the pressure transmitted from the pressure gauge is equal to or greater than a predetermined pressure (for example, any one of the pressure value in the range of 0.5 Bar to 5 Bar or 1.5 Bar to 2 Bar) or the temperature transmitted from the temperature sensor is equal to or greater than a predetermined temperature (for example, 100° C. or higher), the control unit 200 may immediately transmit control signals for closing the first shutoff valve 140, closing the second shutoff valve 150 and opening the safety valve 160 to the first shutoff valve 140, the second shutoff valve 150, and the safety valve 160, respectively. Additionally or alternatively, if the voltage of the secondary battery 20 measured by the charge/discharge module 130 is equal to or greater than a predetermined voltage value (for example, 5 V or more), the control unit 200 may automatically and immediately transmit control signals for closing the first shutoff valve 140, closing the second shutoff valve 150 and opening the safety valve 160 to the first shutoff valve 140, the second shutoff valve 150, and the safety valve 160, respectively.

In the device 10 for analyzing the generated gas in the secondary battery of the present invention, the inside of the chamber 100 may be formed in a vacuum state before the experiment so as to derive a more accurate result value. To this end, the device 10 for analyzing the generated gas in the secondary battery may further comprise a vacuum pump (not shown) connected to the chamber 100 to form a vacuum state inside the chamber 100.

Figure 4:
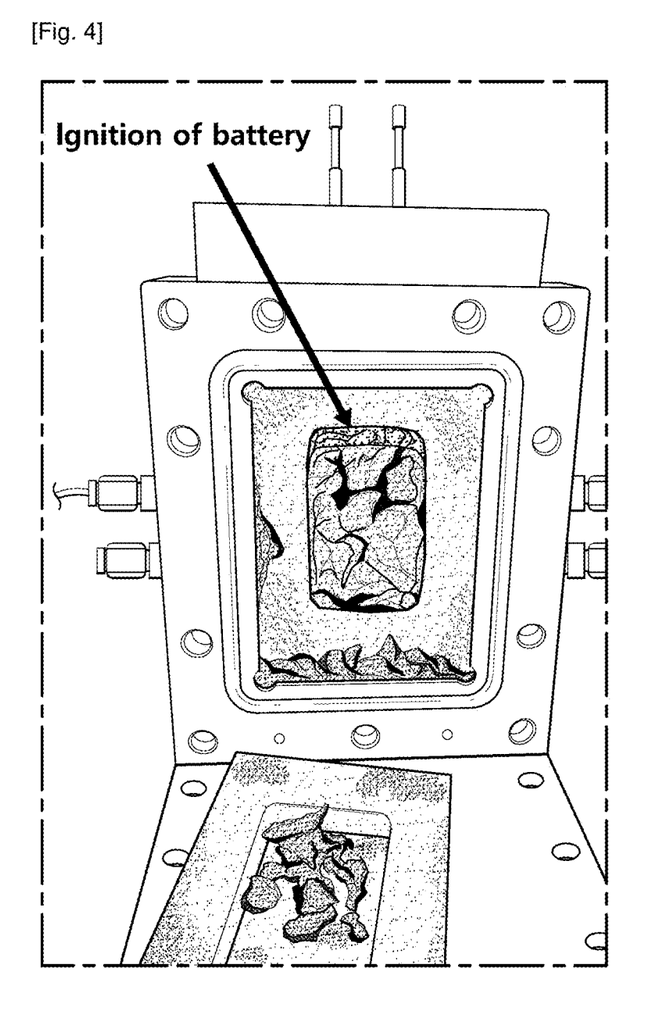
FIG. 4 is a photograph after ignition of the secondary battery 20.

FIG. 4 is a photograph after the secondary battery 20 is ignited.

Figure 5:
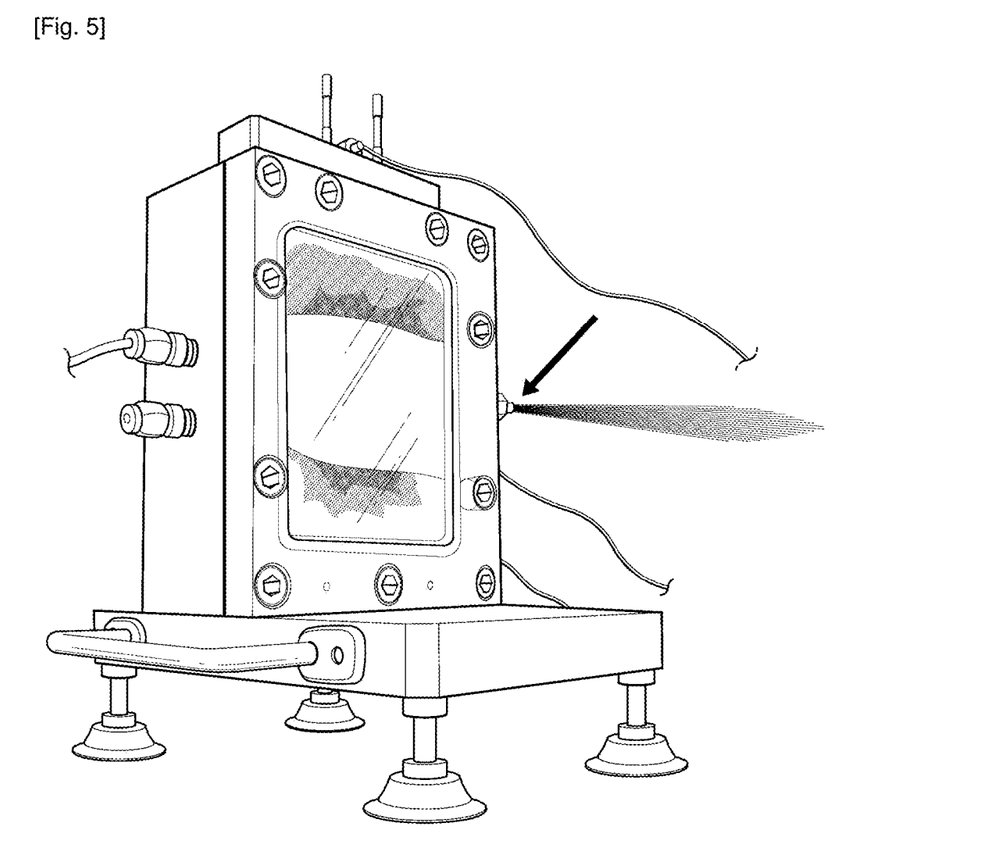
FIG. 5 is a photograph showing a case in which dust, flame, and high-pressure gas are ejected to the analysis module due to ignition or explosion of the secondary battery 20 when the safety valve 160 is not provided.

FIG. 5 is a photograph showing a case in which dust, flame, and high-pressure gas are ejected to the analysis module due to ignition or explosion of the secondary battery 20 when the safety valve 160 is not provided.

Hereinafter, in the analysis of the generated gas in the secondary battery in the device 10 for analyzing the generated gas in the secondary battery of the present invention, the operation of the first shutoff valve 140, the second shutoff valve 150, and the safety valve 160 are described as follows.

1. In the chamber 100, by the flow of the fluid provided from the induction medium supply module 110 into the chamber 100 during the real-time analysis of the generated gas of the secondary battery 20 before the ignition or explosion of the secondary battery 20, the pressure in the chamber 10 is in the range of 1.0 to 1.5 Bar, for example, and fluid flows in the order of the induction medium supply module 110, the chamber 100 and the analysis module 120. The pressure in the chamber 100 may be maintained within a certain range by a mass flow meter (MFC) of the induction medium supply module 110.

At this time, the first shutoff valve 140 connected to the induction medium supply module 110 and the second shutoff valve 150 connected to the analysis module 120 are in an open state, and the safety valve 160 is in a closed state. The generated gas in the secondary battery 20 may be analyzed by the analysis module 120 while charging and discharging the secondary battery 20 by the charge/discharge module 130. Information about the pressure of the surface of the secondary battery 20 or inside the chamber 100 measured by the pressure gauge provided in the chamber 100 and the temperature of the surface of the secondary battery 20 or inside the chamber 100 measured by the temperature sensor is transmitted to the control unit 200 and a data storage device in real time or at a predetermined time interval.

2. When ignition or explosion occurs in the secondary battery 20 due to an abnormal reaction due to overcharge or high temperature of the secondary battery 20, the pressure in the chamber 100 increases, so that the pressure in the chamber 100 becomes the maximum value (that is, the predetermined pressure) of the range of the pressure at the time of analysis of generated gas, for example, the value of one or more of the pressure value of the range of 1.5 Bar to 2 Bar or of at least 1.5 Bar. When a pressure equal to or greater than the predetermined pressure is detected by the pressure gauge provided in the chamber 100, a signal indicating that the pressure equal to or greater than the predetermined pressure is detected from the pressure gauge is immediately transmitted to the control unit 200.

At this time, the first shutoff valve 140 and the second shutoff valve 150 are automatically closed, and the safety valve 160 is automatically opened. Automatic opening and closing of these valves may be automatically operated by direct contact with the high-pressure gas due to ignition, explosion of the secondary battery, or may be automatically controlled by the control unit 200 through a separate drive source. Accordingly, the flame, dust, and high-pressure gas due to ignition or explosion of the secondary battery 20 in the chamber 100 are released to the outside through the open safety valve 160, and a fluid of flow from the chamber 100 to the induction medium supply module 110 and fluid flow from the chamber 100 to the analysis module 120 is blocked, so that the equipments of the induction medium supply module 110 and the analysis module 120 can be protected.

According to the present invention, by providing the first shutoff valve 140 connected to the induction medium supply module 110 and the second shutoff valve 150 connected to the analysis module 120, which are automatically closed, and the safety valve 160 connected to the outside, which is automatically opened, it is possible to minimize the risk of damage to the induction medium supply module 110 and the analysis module 120 due to ignition or explosion of the secondary battery 20, and also to ensure the safety of the user (researcher, etc.) of the device 10.

In addition, according to the related art without the first shutoff valve 140, the second shutoff valve 150, and the safety valve 160, the analysis was performed in an environment in which the secondary battery 20 is not overcharged or not exposed to a high temperature environment in order to avoid ignition or explosion of the secondary battery 20. That is, there is a limit that the generated gas in the secondary battery 20 can be analyzed only under an environment below a predetermined charging voltage or a predetermined temperature.

However, according to the present invention, since the induction medium supply module 110, the analysis module 120, and the like can be protected even in the event of ignition or explosion of the secondary battery 20, there is an advantage that the analysis can be performed up to the point of ignition or explosion of the secondary battery 20 (more precisely, just before ignition or explosion). Accordingly, according to the present invention, since the analysis can be performed up to the point of ignition or explosion of the secondary battery 20, there is an advantage that it can be applied to the experiment on the situation that the secondary battery 20 is ignited or exploded or the safety evaluation experiment of the secondary battery 20. For example, in the past, analysis equipment for gas generated during charging and discharging of the secondary battery 20 and equipment for evaluating stability of the secondary battery 20 were separately provided. However, according to the present invention, it is possible to analyze the generated gas during charging and discharging of the secondary battery 20 and to evaluate stability of the secondary battery 20 with a single device, thereby enabling more efficient experiments and reducing costs. In addition, according to the type of the secondary battery 20 or the experimental environment, if the secondary battery 20 has little impact due to ignition or explosion so that there is no damage to the experimental equipment, the operation time of the first shutoff valve, the second shutoff valve, and the safety valve is delayed and thus analysis can be performed until after the ignition and explosion of the secondary battery 20. Thus, the analysis can be performed up to a certain time after ignition. If the valves should be operated by the time of ignition or explosion of the secondary battery 20 (more precisely, just before the ignition or explosion), the valves should be operated within a few seconds. If the analysis is to be carried out until after the ignition or explosion of the secondary battery 20, the present invention can be applied even several minutes to several hours after the ignition or explosion of the secondary battery 20.

It will be appreciated that the technical configuration of the present invention described above may be embodied in other specific forms by those skilled in the art without changing the technical spirit or essential features of the present invention. Therefore, it is to be understood that the embodiments described above are exemplary and not limiting in all respects. In addition, the scope of the present invention is indicated by the appended claims rather than the detailed description above. In addition, it should be construed that all changes or modifications derived from the meaning and scope of the claims and equivalent concepts thereof are included in the scope of the present invention.

INDUSTRIAL AVAILABILITY

According to the present invention, there is provided a device for analyzing a generated gas in a secondary battery in real time up to the point of ignition and explosion of the secondary battery, while securing researchers' safety and protecting an analytical device of the generated gas in the secondary battery from the risk of battery ignition and explosion.

Furthermore, in addition to the real-time analysis of the generated gas in the secondary battery, it can be applied to experiments related to safety evaluation (overcharge, high temperature exposure, etc.) and analysis of the secondary battery until after ignition and explosion.

What is claimed is:

1. A device for analyzing a gas generated in a secondary battery, the device comprising:
   a chamber configured to receive the secondary battery mounted therein;
   an induction medium supply module configured to generate a flow of an induction medium into the chamber; and
   an analysis module configured to analyze the gas introduced into the analysis module by the flow of the induction medium,
   wherein the chamber comprises:
   an inlet in fluid communication with the induction medium supply module;
   an outlet in fluid communication with the analysis module; and
   a safety valve configured to release flame, dust, and the gas generated in the secondary battery during explosion or ignition of the secondary battery to an outside of the device,
   further comprising a first shutoff valve connected between and in fluid communication with the inlet and the chamber; and a second shutoff valve connected between and in fluid communication with the outlet and the chamber,
   wherein the first shutoff valve is configured to shut off a first flow of the gas from the chamber to the induction medium supply module when the secondary battery is exploded or ignited, and the second shut-off valve is configured to shut off a second flow of the gas from the chamber to the analysis module when the secondary battery is exploded or ignited.

2. The device according to claim 1, wherein the first shutoff valve and the second shutoff valve are configured to be switched from an open state to a closed state at a shutoff pressure equal to or greater than a predetermined pressure, and the safety valve is configured to be switched from a closed state to an open state at a release pressure equal to or greater than the predetermined pressure.

3. The device according to claim 2, wherein the first shutoff valve and the second shutoff valve are configured to be automatically switched from the open state to the closed state when the gas has the shutoff pressure equal to or greater than the predetermined pressure, and the safety valve is configured to be automatically switched from the closed state to the open state when the gas of has the release pressure equal to or greater than the predetermined pressure.

4. The device according to claim 2, further comprising:
   a pressure gauge configured to measure a first pressure of a surface of the secondary battery or a second pressure inside the chamber; and
   a control unit configured to immediately transmit control signals for closing the first shutoff valve, closing the second shutoff valve and opening the safety valve to the first shutoff valve, the second shutoff valve, and the safety valve, respectively, upon receiving a signal indicating that the first pressure or the second pressure measured by the pressure gauge is equal to or greater than the predetermined pressure, wherein when the control signals are received, the first shutoff valve and the second shutoff valve are switched to a closed state and the safety valve is switched to an open state.

5. The device according to claim 1, further comprising:
a temperature sensor configured to measure a first temperature of a surface of the secondary battery or a second temperature inside the chamber; and
a control unit configured to immediately transmit control signals for closing the first shutoff valve, closing the second shutoff valve and opening the safety valve to the first shutoff valve, the second shutoff valve, and the safety valve, respectively, upon receiving a signal indicating that the first temperature or the second temperature measured by the temperature sensor is equal to or greater than a predetermined temperature,
wherein, when the control signals are received, the first shutoff valve and the second shutoff valve are switched to a closed state and the safety valve is switched to an open state.

6. The device according to claim 1, wherein the chamber further comprises charging/discharging terminals configured to be electrically connected to electrodes of the secondary battery, and
wherein the device further comprises a charge/discharge module configured to be electrically connected to the electrodes of the secondary battery through the charging/discharging terminals to charge/discharge the secondary battery.

7. The device according to claim 1, wherein the chamber comprises a chamber body configured to receive the secondary battery mounted therein and which has a cuboid shape with an open front portion and a chamber cover adapted to shield the open front portion,
wherein the inlet is disposed on a first side of the chamber body, the outlet is disposed on a second side of the chamber body, and the safety valve is disposed at a center of the chamber body.

8. The device according to claim 2, wherein the predetermined pressure is between 0.5 Bar and 5 Bar.

* * * * *